United States Patent [19]

Abraham, Jr. et al.

[11] Patent Number: 4,925,998

[45] Date of Patent: May 15, 1990

[54] PROCESS FOR DEHYDROHALOGENATING AROMATIC HALIDES

[75] Inventors: Thomas J. Abraham, Jr., Knoxville; Eric J. Fugate, Jonesborough; Guy R. Steinmetz; Martin D. Dolfi, both of Kingsport, all of Tenn.

[73] Assignee: Eastman Kodak Company, Rochester, N.Y.

[21] Appl. No.: 290,678

[22] Filed: Dec. 27, 1988

[51] Int. Cl.$^5$ ............................................. C07C 1/20
[52] U.S. Cl. ................................. 585/469; 208/262.5
[58] Field of Search ................... 585/469; 208/262.5

[56] References Cited

U.S. PATENT DOCUMENTS 3,493,626  2/1970  Zorm et al. ........................ 585/469
3,595,931  7/1971  Hay et al. ........................ 208/262.5

FOREIGN PATENT DOCUMENTS 1353005  5/1974  United Kingdom ................ 585/469

OTHER PUBLICATIONS

P. N. Rylander, Hydrogenation Methods, Academic Press (1985), pp. 148–156.

*Primary Examiner*—Curtis R. Davis
*Attorney, Agent, or Firm*—J. Frederick Thomsen; William P. Heath, Jr.

[57] ABSTRACT

Disclosed is a process for dehydrohalogenating an aromatic bromide or iodide by contacting the aromatic halide with hydrogen at elevated pressure in the presence of an alkyl halide-forming compound and a Group VIII metal catalyst. The presence of the alkyl halide-forming compound, such as an alkanol, diol, triol or derivative thereof, facilitates the dehydrohalogenation reaction and permits the recovery of the halogen ad alkyl halides from which the bromide and iodide values can be economically recovered.

22 Claims, No Drawings

PROCESS FOR DEHYDROHALOGENATING AROMATIC HALIDES

This invention relates to a novel process for the dehydrohalogenation of aromatic halides. More particularly, this invention pertains to a process for treating a mixture of mono- and poly-halo aromatic compounds with hydrogen in the presence of a catalyst and certain halogen acceptors to obtain a product mixture of dehalogenated aromatic compounds and an alkyl iodide.

In many processes wherein the objective is to halogenate an aromatic compound to produce a specific aromatic halide, undesired isomers and/or polyhalo compounds are produced as by-products. The recovery of the halogen values and recycle of the aromatic compound reactant in a useful form is desirable, if not essential, for both economic and environmental reasons. Such recovery is particularly important in the manufacture of aromatic iodides such as 2,6-diiodonaphthalene which is useful for preparing 2,6-naphthalenedicarboxylic acid and esters thereof. In addition to 2,6-diiodonaphthalene, the oxyiodination process described in U.S. Pat. No. 4,746,758 also produces monoiodonaphthalenes, undesired isomers of diiodonaphthalene, triiodonaphthalenes, and other polyiodonated naphthalenes.

The dehydrohalogenation of aromatic halides with hydrogen in the presence of Group VIII metal catalysts is well known in the art as is shown by P. N. Rylander, Hydrogenation Methods, Academic press (1985) pages 148–156. The known dehydrohalogenation processes generally suffer from one or more disadvantages such as rapid poisoning of the Group VIII metal catalyst, the necessity of high temperatures, coupling of the aromatic halide and hydrogen transfer which may result in Scholl product formation. The recycle of halogen also is a frequent disadvantage due to the problems associated with the handling of elemental halogen or their protic acids which are extremely corrosive. Certain processes employ Bronsted bases such as alkali and alkaline earth hydroxides, acetates, alkoxides or amines to react with the hydrogen halide to limit corrosion and catalyst activity problems. However, the use of Bronsted bases results in the halogen values being converted to salts from which the halogen cannot be recovered economically.

The reaction of aromatic halides with hydrogen in the presence of Group VIII metal catalysts according to known procedures using moderate temperatures and pressures gives little or no conversion to the corresponding unsubstituted aromatic compound and mono-halo aromatic compound. At the high temperatures which are required to produce high conversions, coupling reactions occur to form bi-aromatic and halo-bi-aromatic compounds, e.g., biphenyl, binaphthyl and mono-iodinated compounds thereof, in addition to other Scholl products which are insoluble in the reaction mixture. These side-reaction products can result in equipment fouling.

We have discovered a process for dehydrohalogenating aromatic halides which comprises contacting a reactant comprising one or more aromatic halides, including mono- and poly-halo aromatic compounds, with hydrogen in the presence of a Group VIII metal catalyst and a compound capable of forming an alkyl halide in conjunction with the dehydrohalogenation reaction under dehydrohalogenation conditions of temperature and pressure. The process not only results in the dehydrohalogenation of aromatic halides in high yields and at excellent rates of conversion but also produces an alkyl halide from which the halogen values can be economically recovered. The alkyl iodide is relatively volatile and thus can be recovered simply by flashing it from the dehydrohalogenation product mixture. In addition to permitting the recovery of halogen values at reasonable cost, our process also is advantageous in that it requires lower temperatures to produce results equivalent to those accomplished through the use of known methods. The use of lower temperatures in turn reduces the extent of side-reactions. As used herein, the term "halide" refers to bromide and, especially, iodide ion. Our process is particularly useful for the dehydroiodonation of a reactant comprising a mixture of mono- di- and triiodonaphthalenes.

The aromatic halide reactant which may be used in our process may be mono- or poly-halo, e.g. di- tri- and tetra-halo aromatic compounds. The aromatic nucleus or moiety can contain from 5 to 18 carbon atoms and may be carbocyclic aromatic such as benzene, biphenyl, terphenyl, naphthalene, anthracene, etc. In addition to one or more bromine or iodine atoms, the aromatic moiety may be substituted by various substituents inert or relatively inert under the conditions employed in our process. Examples of such substituents include alkyl of up to about 12 carbon atoms such as methyl, ethyl isobutyl, hexyl, 2-ethylhexyl, nonyl, decyl, dodecyl, etc.; cycloalkyl of about 5 to 12 carbon atoms such as cyclopentyl, cyclohexyl, 4-butylcyclohexyl, etc.; hydroxy; alkoxy of up to about 12 carbon atoms such as methoxy, ethoxy, propoxy, butoxy, octyloxy, etc.; halogen such as chloro; alkloxycarbonyl of from 2 to about 8 carbon atoms such as methoxycarbonyl, ethoxycarbonyl, butoxycarbonyl, hexyloxycarbonyl, etc.; carboxyl; cyano; alkenyl of 2 to about i2 carbon atoms such as vinyl, allyl, etc.; formyl; alkanoyl of 2 to about 8 carbon atoms such as acetyl, propionyl, butyryl, hexanoyl, etc.; alkanoylamido of 2 to about 8 carbon atoms such as acetamido, butyramido, etc.; aroylamido such as benzamido; alkylsulfonyl of up to about 8 carbon atoms such as methylsulfonyl, hexylsulfonyl, etc.; and alkylsulfonamido of up to about 8 carbon atoms such as methanesulfonamido, butanesulfonamido, etc.

The preferred reactants are benzene bromides, benzene iodides, naphthalene bromides and naphthalene iodides, i.e., mono- and poly-bromo benzenes and naphthalenes, mono- and poly-iodo benzenes and naphthalenes and mixtures thereof. Due to their greater reactivity when compared with the analogous bromo and, especially, chloro compounds, the benzene iodides and naphthalene iodides are particularly preferred reactants. The varying reactivities of the halo-aromatic compounds can be used to selectively dehydrohalogenate aromatic compounds substituted with different halide ions. Specific examples of the aromatic iodide reactants include iodobenzene, isomers of diiodobenzene, triiodobenzene, iodotoluene, iodophenol, iodoanisole, iodoacetophenone, diiodobiphenyl, chloroiodobenzene, bromoiodobenzene, diiodonaphthalene, triiodonaphthalene and the various isomers of such compounds.

The aromatic halide reactants are known compounds or mixtures of compounds and/or can be prepared according to published procedures. A number of such process are disclosed in T. Hudlicky et al. *The Chemistry of Halides, Pseudohalides and Azides*, Supplement D, Part 2, 1142-1158, J. Chem. Soc., 1952, 150, European Patent Application Nos. 181,790 and 183,579, Japanese Patent No. 58/77830, Japanese patent Application No. 57/77,631 and Bull. Chem. Soc. Japan, 47, 147 (1974).

Our process is carried out in the presence of a compound capable of forming an alkyl halide under the dehydrohalogenation conditions. The alkyl halide-forming compound may be an alcohol, including both mono- and poly-hydric alcohols such as alkanols, diols and triols, and ethers and carboxylic acid esters thereof. Typical alkyl halide-forming compounds have the general formula

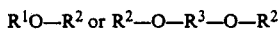

wherein
$R^1$ is alkyl of up to about 12 carbon atoms;
$R^2$ is hydrogen, alkyl of up to about 12 carbon atoms or alkanoyl, i.e., alkyl carboxylic acid acyl, of up to about 8 carbon atoms; and
$R^3$ is alkylene of up to about 8 carbon atoms. Examples of the alcohols which may be used include methanol, ethanol, propanol, butanol, pentanol, hexanol, 2-ethylhexanol, octanol, decanol, 1,2-ethanediol, diethylene glycol, glycerin nd the like. Esters of such alcohols and carboxylic acids such as formic, acetic, proprionic, butyric, isobutyric, valeric, caproic and pelargonic acids are examples of the esters which may be used as the alkyl halide-forming compound. Examples of suitable ethers include dimethyl ether, diethyl ether, dipropyl ether, dibutyl ether, dipentyl ether, dihexyl ether, diheptyl ether, dioctyl ether, didecyl ether, dibenzyl ether dioxane, anisole and mixed dialkyl ethers.

The alkanols of up to about 4 carbon atoms are the preferred alkyl halide-forming compounds. Methanol is particularly preferred since it is the least expensive and produces methyl iodide which is the most volatile of the alkyl iodides.

Normally, at least one mole equivalent of alkyl halide-forming compound should be used for each mole equivalent of aromatic halide reduced. Typically, the alkyl halide-forming compound, preferably methanol, is present in an amount which is about 100 to 10,000 mole percent greater than the moles of compounds constituting the aromatic halide reactant.

The process provided by our invention may be carried out in the presence of an organic solvent depending on the conditions and apparatus employed. Examples of such solvents include aliphatic, alicyclic and aromatic hydrocarbons such as benzene, toluene, the xylenes, hexane, heptane, chlorobenzene, ethylene dichloride, methylchloroform, naphthalene and the like. The use of a solvent, particularly one that is different from the reactant employed in or the product(s) obtained from the process, is not essential.

Palladium, platinum, rhodium, nickel, ruthenium, iridium and mixtures thereof are examples of the Group VIII metal catalysts which may be used as the zero-valent metal or in the form of various salts or complexes which can be reduced to an active catalyst. The catalysts may be one of the aforesaid Group VIII metals deposited on a suitable support or carrier such as carbon, alumina, crystalline or amorphous silica-alumina, barium sulfate or zinc oxide. The preferred catalyst is palladium, particularly palladium metal deposited on a support such as carbon.

The catalytically-effective amount of the catalyst can vary substantially depending on a number of factors such as the particular metal used, the surface area of the catalyst, the reaction conditions, the conversion rate and yield desired, the mode of operation and the like. For example, the concentration of the catalytic metal in the reaction mixture may be within the range of about 0.0001 to 10.0 mole percent, preferably 0.001 to 0.500 mole percent, based on the moles of aromatic halide reactant. However, in certain modes of operation such as in a continuous process using a fixed-bed catalyst, the amounts of catalyst and reactant present is difficult if not impossible to determine.

The process of our invention is carried out under a hydrogen pressure which is sufficient to dehalogenate the aromatic halide and effect formation of an alkyl halide. The hydrogen employed may be essentially pure or it may contain other gases such as carbon dioxide, methane and other compounds typically produced by synthesis gas plants. Normally, the hydrogen used will be at least 50 pure but could be lower depending upon the amount of gas recycled back to the process.

The temperature and pressure required by our process can be varied considerably since they not only are interdependent but also depend on other process variables such as the particular catalyst, catalyst concentration, mode of operation and reactant(s) used and the product(s) desired. While the process can be carried out at pressures (total) as low as ambient pressure and as high as high as 10,000 psig, conversion rates at ambient pressure usually may be unacceptably low while the cost of utilities and equipment required prohibit the use of such high pressures. Thus, the dehydrohalogenation-effective pressure normally is in the range of about ambient to 4000 psig, preferably in the range of about 50 to 1000 psig. Normally, our process is carried out at a temperature of about 75° to 250° C. although temperatures as low as 50° C. and as high as 300° C. may be used. The preferred temperature range is from about 100° to 170° C.

To permit the recovery of halogen as an alkyl halide, our process should be carried out in the absence of any significant amount of basic materials. Examples of the basic materials which should be excluded include amines, particularly tertiary amines, metal hydroxides, metal alkoxides and metal salts of weak acids, e.g., metal carboxylates. Such basic materials combine preferentially with the halogen and thus interfere with the formation of an alkyl halide.

The process provided by our invention may be carried out in a batch, semi-continuous or continuous manner. In batch operation a slurry of the catalyst in the mixture of mono- and poly-halo aromatics and alkanol is fed to a pressure vessel equipped with means for agitation The pressure vessel then is sealed and pressurized, e.g., to a pressure of 50 psig, with hydrogen. The contents of the vessel are then brought to the desired temperature followed by pressurization of the vessel with hydrogen to the reaction pressure with hydrogen being adding continuously to maintain the predetermined process pressure. At the completion of the dehydrohalogenation run, the temperature is reduced, for example, to a temperature at which most or all of the alkyl halide may be flashed from the reaction mixture when the pressure is released. The catalyst may be separated by filtration and the product mixture separated into its various components, for example, by selective crystallization or distillation.

Continuous operation can utilize several types of reactors. One type of operation utilizes a fixed catalyst bed using a larger particle size of catalyst, e.g., catalyst pellets. The catalyst may be fixed in a tubular or columnar, high pressure reactor and a preheated mixture of the reactant and alkanol, dissolved in an inert solvent if desired, slowly fed continuously to the bed at elevated pressure and temperature. The product mixture is removed continuously from the base of the reactor. Another type of reactor utilizes a continuous stirred tank using catalyst pellets or a continuous feed of an appropriate salts or complex of the Group VIII metal.

Our invention is further illustrated by the following examples. The temperatures and pressures given in the examples are °C. and total pounds per square inch gauge unless specified otherwise.

In the procedure used in Examples 1-25 and Comparative Examples, the materials used are loaded into a 330 mL autoclave constructed of Hastelloy B2 alloy and designed to operate in a rocking mode. The autoclave is pressurized to 200 psig with hydrogen at room temperature and then the hydrogen is vented and the autoclave is sealed. The autoclave then is pressurized to 50 psig with hydrogen and heated and rocked until the desired reaction temperature is reached at which time additional hydrogen is added to increase the autoclave internal pressure to the predetermined value. This point in the procedures represents the commencement of the time or period of the reaction. Reactor pressure is maintained by adding hydrogen at the rate at which it is consumed by the reactants. The hydrogen used is essentially pure. At the end of the reaction time, the autoclave is cooled by a stream of cold air to approximately 25° C. The pressure then is released and the contents of the autoclave are isolated by decantation. p-Xylene is used as an autoclave wash to recover trace amounts of product remaining in the autoclave. The reaction product and wash are combined and filtered to separate the catalyst from the reaction mixture. The solids isolated by filtration are analyzed only if they exceed the initial catalyst charge. For some of the examples the isolation procedure described resulted in the loss of a significant amount of the very volatile methyl iodide reaction product. Samples of the filtrate and, when formed, the solids obtained in each example are analyzed by gas chromatographic methods. In certain of the examples the filtrate consisted of two phases, both of which were analyzed, due to water formed in the dehydrohalogenation reaction. The analytical values for each product component present in the solids and/or filtrate were combined and converted to total millimoles (mmol).

EXAMPLES 1-6

In Examples 1-6 the reactant consisted of a mixture comprising (by gas chromatographic analyses) naphthalene, 2-iodonaphthalene, 1-iodonaphthalene, diiodonaphthalene isomers, triiodonaphthalene isomers, binaphthyl isomers and iodobinaphthyl isomers. The reactant mixture was obtained by the oxyiodination of reagent grade naphthalene according to the process described in U.S. Pat. No. 4,746,758 followed by the removal of most of the 2,6- and 2,7-diiodonaphthalene by selective crystallization.

In each example, the reactant mixture was dehydrohalogenated at 150° C. and 1000 psig for 4 hours in the presence of methanol and a Group VIII metal catalyst. The amount (g) of the reactant mixture (Reactant) and methanol (MeOH) and the Group VIII metal catalyst used in each of Examples 1-6 are set forth below.

| Example | Reactant | MeOH | | Catalyst |
|---------|----------|------|------|----------|
| 1 | 100.52 | 47.66 | 1.01 | 5.0% Palladium on sulfided carbon |
| 2 | 101.00 | 47.89 | 1.51 | 1.0% Palladium on alumina |
| 3 | 101.20 | 47.53 | 3.04 | 0.5% Palladium on carbon |
| 4 | 101.54 | 48.23 | 1.03 | 5.0% Palladium on barium sulfate |
| 5 | 101.22 | 47.75 | 1.98 | 0.5% Platinum on alumina |
| 6 | 100.60 | 48.16 | 1.00 | Raney nickel |

The mmol of naphthalene (Naph.), 2-iodonaphthalene (2-I-Naph.), 1-iodonaphthalene (1-I-Naph.), diiodonaphthalene isomers (Di-I-Naph.), triiodonaphthalene isomers (Tri-I-Naph.), binaphthyl isomers (Binaph.) and iodobinaphthyl (I-Binaph.) contained in the reactants and products are given in Table I. The amount of methyl iodide produced in each of Example 1-6 was not determined (ND).

EXAMPLES 7-17

In Examples 7-17 the reactant consisted of a mixture comprising naphthalene, 2-iodonaphthalene, 1-iodonaphthalene, diiodonaphthalene isomers and triiodonaphthalene isomers. The reactant mixture was obtained by the oxyiodination of freshly distilled naphthalene according to the process described in U.S. Pat. No. 4,746,758 and contained no binaphthyl or iodobinaphthyl isomers. In each example, the reactant mixture was dehydrohalogenated at various temperatures and pressures using varying reaction times in the presence of methanol and 5.0% palladium on carbon (0.31±0.01 g). The amounts (g) of reactant mixture (Reactant) and methanol (MeOH), the reaction conditions and the reaction times (Time, minutes) used in Examples 7-15 are set forth below.

| Example | Temp. | Press. | Time | Reactant | MeOH |
|---------|-------|--------|------|----------|------|
| 7 | 150 | 1000 | 60 | 25.20 | 58.66 |
| 8 | 150 | 500 | 120 | 50.06 | 117.92 |
| 9 | 150 | 500 | 60 | 25.05 | 118.03 |
| 10 | 135 | 750 | 90 | 37.58 | 89.78 |
| 11 | 120 | 1000 | 60 | 25.08 | 118.03 |
| 12 | 120 | 500 | 120 | 50.01 | 58.65 |
| 13 | 120 | 1000 | 120 | 50.09 | 117.00 |
| 14 | 120 | 1000 | 60 | 50.03 | 58.89 |
| 15 | 120 | 350 | 60 | 25.06 | 118.05 |
| 16 | 170 | 700 | 60 | 25.09 | 118.79 |
| 17 | 170 | 500 | 60 | 25.37 | 118.40 |

The mmol of naphthalene, 2-iodonaphthalene, 1-iodonaphthalene, diiodonaphthalene isomers, triiodonaphthalene isomers and binaphthyl isomers present in the reactant and the product for each example are shown in Table I. Only the mmol of methyl iodide present in the product is shown in Table I since none is present in the reactant.

EXAMPLES 18-24

Examples 18-24 employed the same reactant as was used in Examples 7-17. In each example, the reactant mixture was dehydrohalogenated at 120° C. and varying pressures using 90-minute reaction times in the presence of methanol and 5.0% palladium on carbon (0.15 g). The amounts (g) of reactant mixture (Reactant) and methanol (MeOH) and the pressure used in the examples are shown below.

| Example | Press. | Reactant | MeOH |
|---|---|---|---|
| 18 | 600 | 37.67 | 90.41 |
| 19 | 600 | 25.32 | 59.20 |
| 20 | 600 | 50.02 | 118.69 |
| 21 | 350 | 50.20 | 59.14 |
| 22 | 350 | 50.16 | 118.13 |
| 23 | 850 | 50.25 | 118.32 |
| 24 | 850 | 25.32 | 59.05 |

The mmol of naphthalene, 2-iodonaphthalene, 1-iodonaphthalene, diiodonaphthalene isomers, triiodonaphthalene isomers, binaphthyl isomers and iodobinaphthyl isomers present in the reactant and the product for each example are shown in Table I. The mmol of methyl iodide present in the product also is given in Table I.

EXAMPLE 25

1-Bromonaphthalene (25.02) was dehydrohalogenated in the presence of methanol (80.02 g) and 5.0% palladium on carbon (0.30 g) for 1 hour at 150° C. and 1000 psig. Analysis of the reaction product showed complete dehydrohalogenation of the 1-bromonaphthalene to naphthalene with a trace of tetrahydronaphthalene.

EXAMPLES 26-29

In the procedure used in Examples 26-29 a 330 mL rocking type autoclave constructed of Hastelloy C-276 alloy was charged with the materials used, sealed, purged with nitrogen, pressurized with hydrogen to 500 psig and checked for leaks, vented, pressurized with hydrogen or a combination of hydrogen and carbon dioxide to 500 psig and then heated with rocking to the reaction temperature. This point in the procedure marked the commencement of time or period of the reaction. The reaction was carried out for 1 or 4 hours with no additional was being added. At the end of the reaction time, the autoclave is cooled by a stream of cool air to approximately 25° C. The pressure is then released and the contents of the autoclave were unloaded. In Example 26 in which no solvent was used. 50.0 g of p-xylene was added to the product mixture. The resulting mixture is filtered to separate the catalyst and the reaction product was analyzed as described hereinabove. In Examples 27 and 28 in which a co-solvent was used, the products were obtained in two liquid phases. In Example 29 in which an inert gas (carbon dioxide) was used, 25.0 g of p-xylene was added to the product and the mixture obtained was filtered to give a 2-phase filtrate. The mmol of naphthalene, 2-iodonaphthalene, 1-iodonaphthalene, diiodonaphthalene isomers, triiodonaphthalene isomers, binaphthyl isomers and iodobinaphthyl isomers present in the reactant and the product for each example are shown in Table I. The mmol of methyl iodide in the product also is given in Table I.

In Examples 26-28 the reactant mixture used was obtained by the oxyiodination of freshly distilled naphthalene according to the process described in U.S. Pat. No. 4,746,758 and contained no binaphthyl or iodobinaphthyl isomers. In each example, the reactant mixture (15.0 g) was dehydrohalogenated at 120° C. and 600 psig for 1 hour in the presence of methanol and/or co-solvent and 5.0% palladium on carbon (1.5 g). The amounts of methanol and co-solvent employed were:

| Example | MeOH | Heptane | p-Xylene |
|---|---|---|---|
| 26 | 125.0 | 0.0 | 0.0 |
| 27 | 15.0 | 125.0 | 0.0 |
| 28 | 15.0 | 0.0 | 110.0 |

In Example 29 the reactant mixture (15.0 g) used was obtained by the oxyiodination of reagent grade naphthalene according to the process described in U.S. Pat. No. 4,746,758 followed by the removal of most of the 2,6- and 2,7-naphthalene by selective crystallization. The dehydrohalogenation was carried out at 150° C. and 1000 psig for 4 hours in the presence of methanol (125.0 g) and 5.0% palladium on carbon (1.5 g). The autoclave was pressurized initially with 400 psig hydrogen and 100 psig carbon dioxide.

COMPARATIVE EXAMPLES 1-4

Comparative Examples 1-4 were carried out using the procedure and reactant mixture employed in Examples 1-6 but in the absence of any alkyl halide-forming compound, i.e., methanol. In each example, the reactant mixture was dehydrohalogenated at various temperatures and pressures for 2 hours in the presence of 0.5% palladium on carbon. The amounts of reactant mixture and catalyst and the reaction conditions used are set forth below.

| Comparative Example | Temp. | Press. | Reactant | Catalyst |
|---|---|---|---|---|
| 1 | 125 | 350 | 100.36 | 5.03 |
| 2 | 150 | 326 | 100.99 | 5.04 |
| 3 | 175 | 322 | 100.92 | 5.02 |
| 4 | 200 | 333 | 100.38 | 5.06 |

The mmol of naphthalene (Naph.), 2-iodonaphthalene (2-I-Naph.), 1-iodonaphthalene (1-I-Naph.), diiodonaphthalene isomers (Di-I-Naph ) and triiodonaphthalene isomers (Tri-I-Naph.) contained in the reactants and products were determined as described above and are given in Table I.

TABLE I

| Example | | Naph. | 2-I-Naph. | 1-I-Naph. | Di-I-Naph. | Tri-I-Naph. | Binaph. | I-Binaph. | MeI |
|---|---|---|---|---|---|---|---|---|---|
| 1 | Reactant | 0.00 | 11.79 | 5.70 | 211.86 | 20.98 | 0.94 | 1.56 | ND |
|   | Product | 93.81 | 32.79 | 53.86 | 9.57 | 4.57 | 1.86 | 1.36 | ND |
| 2 | Reactant | 0.00 | 11.85 | 5.73 | 212.87 | 21.08 | 1.95 | 1.57 | ND |
|   | Product | 28.83 | 27.38 | 23.86 | 130.65 | 14.58 | 1.40 | 1.44 | ND |
| 3 | Reactant | 0.00 | 11.87 | 5.74 | 213.29 | 21.12 | 1.95 | 1.57 | ND |
|   | Product | 21.98 | 50.51 | 41.09 | 85.70 | 5.45 | 1.02 | 1.41 | ND |
| 4 | Reactant | 0.00 | 11.91 | 5.76 | 214.01 | 21.19 | 1.96 | 1.58 | ND |
|   | Product | 113.74 | 18.76 | 51.37 | 5.25 | 4.77 | 1.93 | 1.42 | ND |
| 5 | Reactant | 0.00 | 11.88 | 5.74 | 213.33 | 21.12 | 1.95 | 1.57 | ND |
|   | Product | 7.06 | 38.53 | 27.31 | 143.65 | 12.60 | 1.07 | 1.93 | ND |
| 6 | Reactant | 0.00 | 11.80 | 5.70 | 212.03 | 20.99 | 1.94 | 1.56 | ND |

TABLE I-continued

| Example | | Naph. | 2-I-Naph. | 1-I-Naph. | Di-I-Naph. | Tri-I-Naph. | Binaph. | I-Binaph. | MeI |
|---|---|---|---|---|---|---|---|---|---|
|   | Product  | 0.78   | 15.52 | 8.30  | 194.19 | 18.36 | 0.71 | 0.88 | ND |
| 7 | Reactant | 0.00   | 37.04 | 8.21  | 30.73  | 3.65  | 0.00 | 0.00 | ND |
|   | Product  | 83.90  | 0.00  | 0.00  | 0.00   | 0.00  | 0.00 | 0.00 | 11.10 |
| 8 | Reactant | 0.00   | 73.57 | 16.32 | 61.05  | 7.24  | 0.00 | 0.00 | ND |
|   | Product  | 162.06 | 0.00  | 3.48  | 0.00   | 0.00  | 0.00 | 0.00 | 6.41 |
| 9 | Reactant | 0.00   | 36.82 | 8.17  | 30.55  | 3.62  | 0.00 | 0.00 | ND |
|   | Product  | 76.24  | 0.00  | 0.00  | 0.00   | 0.00  | 0.00 | 0.00 | 47.82 |
| 10 | Reactant | 0.00  | 55.23 | 12.25 | 45.83  | 5.44  | 0.00 | 0.00 | ND |
|   | Product  | 102.50 | 5.07  | 10.67 | 0.00   | 0.00  | 0.00 | 0.00 | 43.27 |
| 11 | Reactant | 0.00  | 36.86 | 8.18  | 30.58  | 3.63  | 0.00 | 0.00 | ND |
|   | Product  | 75.91  | 0.00  | 0.00  | 0.00   | 0.00  | 0.00 | 0.00 | 35.54 |
| 12 | Reactant | 0.00  | 73.50 | 16.30 | 60.99  | 7.23  | 0.00 | 0.00 | ND |
|   | Product  | 69.96  | 57.00 | 25.95 | 5.10   | 0.00  | 0.00 | 0.00 | 53.41 |
| 13 | Reactant | 0.00  | 73.62 | 16.33 | 61.08  | 7.25  | 0.00 | 0.00 | ND |
|   | Product  | 135.67 | 0.00  | 0.00  | 0.00   | 0.00  | 0.00 | 0.00 | 121.70 |
| 14 | Reactant | 0.00  | 73.53 | 16.31 | 61.01  | 7.24  | 0.00 | 0.00 | ND |
|   | Product  | 105.89 | 36.29 | 23.73 | 1.03   | 0.00  | 0.00 | 0.00 | 66.50 |
| 15 | Reactant | 0.00  | 36.83 | 8.17  | 30.56  | 3.63  | 0.00 | 0.00 | ND |
|   | Product  | 54.58  | 14.04 | 10.64 | 0.00   | 0.00  | 0.00 | 0.00 | 62.43 |
| 16 | Reactant | 0.00  | 36.87 | 8.18  | 30.56  | 3.63  | 0.00 | 0.00 | ND |
|   | Product  | 73.97  | 0.00  | 0.00  | 0.00   | 0.00  | 0.00 | 0.00 | 51.46 |
| 17 | Reactant | 0.00  | 37.29 | 8.27  | 30.94  | 3.67  | 0.00 | 0.00 | ND |
|   | Product  | 77.36  | 1.32  | 4.03  | 0.05   | 0.00  | 0.00 | 0.00 | 12.58 |
| 18 | Reactant | 0.00  | 56.82 | 12.86 | 48.05  | 6.70  | 0.00 | 0.00 | ND |
|   | Product  | 26.42  | 59.74 | 19.57 | 11.13  | 0.00  | 0.00 | 0.00 | 39.59 |
| 19 | Reactant | 0.00  | 38.19 | 8.64  | 32.30  | 4.50  | 0.00 | 0.00 | ND |
|   | Product  | 29.05  | 32.35 | 13.28 | 2.71   | 0.00  | 0.00 | 0.00 | 39.39 |
| 20 | Reactant | 0.00  | 75.44 | 17.07 | 63.80  | 8.90  | 0.00 | 0.00 | ND |
|   | Product  | 2.52   | 74.04 | 17.76 | 53.19  | 2.22  | 0.00 | 0.00 | 10.89 |
| 21 | Reactant | 0.00  | 75.72 | 17.14 | 64.03  | 8.93  | 0.00 | 0.00 | ND |
|   | Product  | 8.66   | 65.12 | 16.44 | 38.74  | 1.25  | 0.00 | 0.00 | 9.94 |
| 22 | Reactant | 0.00  | 75.65 | 17.12 | 63.98  | 8.92  | 0.00 | 0.00 | ND |
|   | Product  | 6.00   | 75.55 | 19.48 | 45.07  | 0.86  | 0.00 | 0.00 | 16.08 |
| 23 | Reactant | 0.00  | 75.79 | 17.15 | 64.10  | 8.94  | 0.00 | 0.00 | ND |
|   | Product  | 16.90  | 80.24 | 22.70 | 32.28  | 0.08  | 0.00 | 0.00 | 31.77 |
| 24 | Reactant | 0.00  | 38.19 | 8.64  | 32.30  | 4.50  | 0.00 | 0.00 | ND |
|   | Product  | 19.48  | 38.22 | 13.21 | 6.64   | 0.00  | 0.00 | 0.00 | 37.44 |
| 26 | Reactant | 0.05  | 22.82 | 5.24  | 19.05  | 0.90  | 0.00 | 0.00 | ND |
|   | Product  | 46.04  | 0.00  | 0.00  | 0.00   | 0.00  | 0.00 | 0.00 | 35.65 |
| 27 | Reactant | 0.05  | 22.82 | 5.24  | 19.05  | 0.90  | 0.00 | 0.00 | ND |
|   | Product  | 36.37  | 2.54  | 3.65  | 0.00   | 0.00  | 0.00 | 0.00 | 24.90 |
| 28 | Reactant | 0.00  | 18.97 | 4.62  | 21.07  | 1.55  | 0.00 | 0.00 | ND |
|   | Product  | 42.48  | 0.00  | 1.01  | 0.00   | 0.00  | 0.00 | 0.00 | 41.05 |
| 29 | Reactant | 0.00  | 1.38  | 0.59  | 35.27  | 2.17  | 0.00 | 0.00 | ND |
|   | Product  | 28.53  | 0.38  | 2.62  | 0.00   | 0.00  | 2.29 | 0.00 | 12.08 |
| C-1 | Reactant | 0.78 | 7.07  | 3.14  | 213.58 | 17.28 | ND   | ND   | ND |
|   | Product  | 0.35   | 5.34  | 3.36  | 178.01 | 14.96 | ND   | ND   | ND |
| C-2 | Reactant | 0.79 | 7.12  | 3.46  | 214.92 | 17.38 | ND   | ND   | ND |
|   | Product  | 1.05   | 5.95  | 3.46  | 180.88 | 14.92 | ND   | ND   | ND |
| C-3 | Reactant | 0.79 | 7.11  | 3.46  | 214.77 | 17.37 | ND   | ND   | ND |
|   | Product  | 0.99   | 6.70  | 3.56  | 162.86 | 12.89 | ND   | ND   | ND |
| C-4 | Reactant | 0.78 | 7.07  | 3.44  | 213.62 | 17.28 | ND   | ND   | ND |
|   | Product  | 4.31   | 17.59 | 5.53  | 137.52 | 11.72 | ND   | ND   | ND |

The invention has been described in detail with particular reference to preferred embodiments thereof, but it will be understood that variations and modifications may be effected within the spirit and scope of the invention.

We claim:

1. Process for dehydrohalogenating an aromatic halide which comprises contacting a reactant comprising one or more aromatic halides with hydrogen in the presence of a Group VIII metal catalyst and an alkyl halide-forming compound under dehydrohalogenation conditions of pressure and temperature, wherein the halide is bromide or iodide.

2. Process according to claim 1 wherein the Group VIII metal is palladium, platinum, rhodium, nickel, ruthenium or iridium.

3. Process according to claim 1 wherein the halide is an iodide and the Group VIII metal is palladium.

4. Process according to claim 3 wherein the aromatic halide is iodonaphthalene, diiodonaphthalene, triiodonaphthalene or a mixture thereof.

5. Process according to claim 1 wherein the aromatic halide is iodonaphthalene, diiodonaphthalene, triiodonaphthalene or a mixture thereof and the Group VIII metal catalyst is palladium deposited on a support.

6. Process for dehydrohalogenating an aromatic halide which comprises contacting a reactant comprising one or more aromatic halides with hydrogen in the presence of a palladium catalyst and an alkyl halide-forming compound under dehydrohalogenation conditions of pressure and temperature, wherein the aromatic halide is a benzene bromide, a benzene iodide, a naphthalene bromide, a naphthalene iodide or a mixture thereof.

7. Process according to claim 6 wherein the alkyl halide-forming compound has the formula $$R^1O-R^2 \text{ or } R^2-O-R^3-O-R^2$$

wherein $R^1$ is alkyl of up to about 12 carbon atoms;

R² is hydrogen, alkyl of up to about 12 carbon atoms or alkanoyl, i.e., alkyl carboxylic acid acyl, of up to about 8 carbon atoms; and R³ is alkylene of up to about 8 carbon atoms, the pressure is in the range of about 50 to 1000 psig and the temperature is in the range of about 75° to 250° C.

8. Process according to claim 6 wherein the alkyl halide-forming compound is an alkanol of up to about 4 carbon atoms, the pressure is in the range of about 50 to 1000 psig and the temperature is in the range of about 75° to 250° C.

9. Process according to claim 6 wherein the alkyl halide-forming compound is methanol, the pressure is in the range of about 50 to 1000 psig and the temperature is in the range of about 75° to 250° C.

10. Process according to claim 6 wherein the alkyl halide-forming compound is methanol, the pressure is in the range of about 50 to 1000 psig and the temperature is in the range of about 100° to 170° C.

11. Process according to claim 6 wherein the alkyl halide-forming compound is an alkanol of up to about 4 carbon atoms, the palladium catalyst is palladium on carbon, the pressure is in the range of about 50 to 1000 psig and the temperature is in the range of about 75° to 250° C.

12. Process according to claim 6 wherein the alkyl halide-forming compound is methanol, the palladium catalyst is palladium on carbon, the pressure is in the range of about 50 to 1000 psig and the temperature is in the range of about 75° to 250° C.

13. Process according to claim 6 wherein the alkyl halide-forming compound is methanol, the palladium catalyst is palladium on carbon, the pressure is in the range of about 50 to 1000 psig and the temperature is in the range of about 100° to 170° C.

14. Process for dehydrohalogenating an aromatic iodide which comprises contacting a reactant comprising iodonaphthalene, diiodonaphthalene, triiodonaphthalene or a mixture thereof with hydrogen in the presence of a palladium catalyst and an alkyl halide-forming compound under dehydrohalogenation conditions of pressure and temperature.

15. Process according to claim 14 wherein the alkyl halide-forming compound has the formula

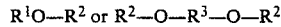

$R^1O-R^2$ or $R^2-O-R^3-O-R^2$ wherein
R¹ is alkyl of up to about 12 carbon atoms;
R² is hydrogen, alkyl of up to about 12 carbon atoms or alkanoyl, i.e., alkyl carboxylic acid acyl, of up to about 8 carbon atoms; and
R³ is alkylene of up to about 8 carbon atoms, the pressure is in the range of about 50 to 1000 psig and the temperature is in the range of about 75° to 250° C.

16. Process according to claim 14 wherein the alkyl halide-forming compound is an alkanol of up to about 4 carbon atoms, the pressure is in the range of about 50 to 1000 psig and the temperature is in the range of about 75° to 250° C.

17. Process according to claim 14 wherein the alkyl halide-forming compound is methanol, the pressure is in the range of about 50 to 1000 psig and the temperature is in the range of about 75° to 250° C.

18. Process according to claim 14 wherein the alkyl halide-forming compound is methanol, the pressure is in the range of about 50 to 1000 psig and the temperature is in the range of about 100° to 170° C.

19. Process according to claim 14 wherein the alkyl halide-forming compound is an alkanol of up to about 4 carbon atoms, the palladium catalyst is palladium on carbon, the pressure is in the range of about 50 to 1000 psig and the temperature is in the range of about 75° to 250° C.

20. Process according to claim 14 wherein the alkyl halide-forming compound is methanol, the palladium catalyst is palladium on carbon, the pressure is in the range of about 50 to 1000 psig and the temperature is in the range of about 75° to 250° C.

21. Process according to claim 14 wherein the alkyl halide-forming compound is methanol, the palladium catalyst is palladium on carbon, the pressure is in the range of about 50 to 1000 psig and the temperature is in the range of about 100° to 170° C.

22. Process for dehydroiodinating an aromatic iodide which comprises contacting a reactant comprising iodonaphthalene, diiodonaphthalene, triiodonaphthalene or a mixture thereof with hydrogen in the presence of palladium on carbon and methanol at a pressure of about 50 to 1000 psig and a temperature of about 100° to 170° C.

* * * * *